United States Patent [19]

Huang et al.

[11] Patent Number: 4,623,627

[45] Date of Patent: Nov. 18, 1986

[54] MONOCLONAL ANTIBODY HAVING SPECIFICITY FOR THE DOUBLE-STRANDED CONFORMATION OF NATIVE DNA AND DIAGNOSTIC METHODS USING SAME

[75] Inventors: Chun-Ming Huang, Cupertino; Stanley N. Cohen, Portola Valley, both of Calif.

[73] Assignee: Cetus Corporation, Emeryville, Calif.

[21] Appl. No.: 524,596

[22] Filed: Aug. 19, 1983

[51] Int. Cl.$^4$ .................. C12N 5/00; C12N 15/00; C12Q 1/68; G01N 33/577
[52] U.S. Cl. ........................ 435/240; 435/6; 435/7; 435/172.2; 435/948; 436/548; 530/387; 530/809; 935/78; 935/103; 935/110
[58] Field of Search .................. 435/6, 7, 68, 172.2, 435/240, 948, 810; 436/508, 513, 540, 548, 815, 501; 260/112 B, 112 R; 935/78, 95, 103, 104, 105, 110; 530/387, 809; 536/27

[56] References Cited

U.S. PATENT DOCUMENTS 4,358,535 11/1982 Falkow et al. .................. 435/6

FOREIGN PATENT DOCUMENTS 0063879 11/1982 European Pat. Off. .

OTHER PUBLICATIONS

Hahn, B. H., et al, *Arthritis and Rheumatism* (1980) 23:942–945.
Tron, F., et al, *J Immun* (1980) 125:2805–2809.
Gilliam, A. C., et al, *J. Immun* (1980) 125:874–885.
Andrzejewski, Jr., C., et al, *J Immun* (1980) 124:1499–1502.
Ballard, D. W., et al, *Molecular Immunology* (1982) 19:793–799.
Koike, T., et al, *Immunology Letters* (1982) 4:93–97.
Lafer, E. M., et al, *PNAS (U.S.A.)* (1981) 78:3546–3550.
Moller, A., et al, *J Biol Chem* (1982) 251:12081–12085.
Ballard, Fed. Proc., 40 (3): 975, Abst. 4221, Mar. 1, 1981.
Tron et al, Clin. Immunol. Immunopathol., 24 (3): 351–360, (1982), Abstract.
Tron et al, Clin. Immunol. and Immunopath., 24:351–360 (1982).
Ballard et al, Molec. Immunol., 19 (6): 793–799 (1982).
Kohler et al, Nature, 256: 495–497 (1975).

Primary Examiner—Esther M. Kepplinger
Attorney, Agent, or Firm—Albert P. Halluin; Thomas E. Ciotti; Janet E. Hasak

[57] ABSTRACT

Monoclonal antibodies having conformation-dependent specificity for native dsDNA, as exemplified by the IgM antibody produced by murine hybridoma ATCC No HB 8329. These antibodies are used to detect DNA duplex formation in DNA hybridization tests.

1 Claim, 3 Drawing Figures

MONOCLONAL ANTIBODY HAVING SPECIFICITY FOR THE DOUBLE-STRANDED CONFORMATION OF NATIVE DNA AND DIAGNOSTIC METHODS USING SAME

DESCRIPTION

1. Technical Field

The invention is in the fields of immunochemistry, nucleic acid chemistry, and immunodiagnostics.

2. Background Art

Many biomedical research and recombinant DNA procedures involve the use of single-stranded DNA (ssDNA) probes to identify particular DNA molecules. The nucleotide sequence of the probe is complementary to part or all of the nucleotide sequence of a strand of the DNA molecule to be identified and the procedures involve hybridizing (annealing) the probe to a denatured (single-stranded) form of the DNA to be identified. Resulting duplexes are detected directly via components (e.g., radioisotopes) of the probe that are per se detectable or indirectly via reactive components of the probe (e.g., biotin or derivatives thereof) that form detectable derivatives. Examples of such procedures are described in U.S. Pat. No. 4,358,535 and European Patent Application No. 82301804.9 (publication no 0063879). A major practical problem in this DNA probe technology lies in the difficulty and expense of incorporating moieties such as radioisotopes or biotin into the complementary ssDNA probe. A main object of the present invention is to avoid this problem and provide a technique for detecting DNA duplexes that does not involve the inclusion of such moieties in the complementary ssDNA probe.

The present invention provides an immunochemical that specifically recognizes the doublestrandedness of native DNA duplexes, namely a monoclonal antibody that has conformation-dependent specificity for native double-stranded DNA (dsDNA). By using this antibody in DNA probe technology, the requisite that the probe DNA itself contain an added detection component is eliminated. The only requisite of the probe DNA is complementarity to the DNA to be identified. Accordingly, a major feature of this invention is that it allows the probe DNA to be produced by cloning single-stranded DNA (ssDNA) using vectors such as M13. Cloning the probe with such single-stranded phage vectors allows excess probe to be used, thereby increasing the sensitivity of duplex detection.

As re.g.ards the monoclonal antibody of the invention, there are numerous prior reports of murine monoclonal antibodies against native DNA. See *Arthritis and Rheumatism* (1980) 23:942–945; *J Immun* (1980) 125:2805–2809; *J Immun* (1980) 125:824–885; *J Immun* (1980) 124:1499–1502; *Molecular Immunology* (1982) 19:793–799; and *Immunology Letters* (1982) 4:93–97. These antibodies were generated by hybridomas made by fusing available murine plasmacytomas with spleen cells from mice (e.g., $F_1$ hybrid New Zealand Black/White mice) that normally produced high titers of anti-dsDNA antibodies. All of the prior anti-DNA monoclonal antibodies have either bound ssDNA preferentially or bound both ssDNA and dsDNA. Since these prior antibodies are not exclusively specific for dsDNA they are unsuitable for detecting duplexes in the above described DNA probe technology.

Polyclonal and monoclonal antibodies against the Z form of DNA have been reported. PNAS (USA) (1981) 78:3546–3550 and *J Biol Chem* (1982) 251:12081–12085.

DISCLOSURE OF THE INVENTION

One aspect of the invention is a monoclonal antibody that has exclusive specificity for the double-stranded conformation of native DNA. This antibody conjugated to a label or a chromatography support are variations of this aspect of the invention.

Another aspect of the invention is hybridoma ATCC HB 8329 which produces a monoclonal (IgM light chain) antibody that has exclusive specificity for the double-stranded conformation of native DNA.

Other aspects of the invention are immune complexes that comprise the above described monoclonal antibody bound to dsDNA. Embodiments of such complexes are binary complexes of dsDNA and labeled conjugates of the monoclonal antibody and ternary complexes of dsDNA, the monoclonal antibody and a labeled antibody against the monoclonal antibody.

Various immunodiagnostic methods are additional aspects of the invention. The common steps in these methods are (1) binding the monoclonal antibody to dsDNA and (2) detecting the resulting complex via a label conjugated to the monoclonal antibody or a label conjugated to an immunochemical bound directly or indirectly to the monoclonal antibody. When used in DNA probe technology to detect a given DNA sequence in a sample, such as a sequence that characterizes a genetic disorder, pathogenic disease, or other medical condition, the binding reaction (step (1) above) will be preceded by the steps of treating the sample to denature any dsDNA contained in it and hybridizing the denatured (single-stranded) DNA with ssDNA probe that is complementary to the given DNA sequence.

The invention also contemplates kits for carrying out such immunodiagnostic methods.

Methods and kits for isolating and/or identifying dsDNA molecules, such as plasmids after denaturing, are also part of the invention.

MODES FOR CARRYING OUT THE INVENTION

Figure 1A:
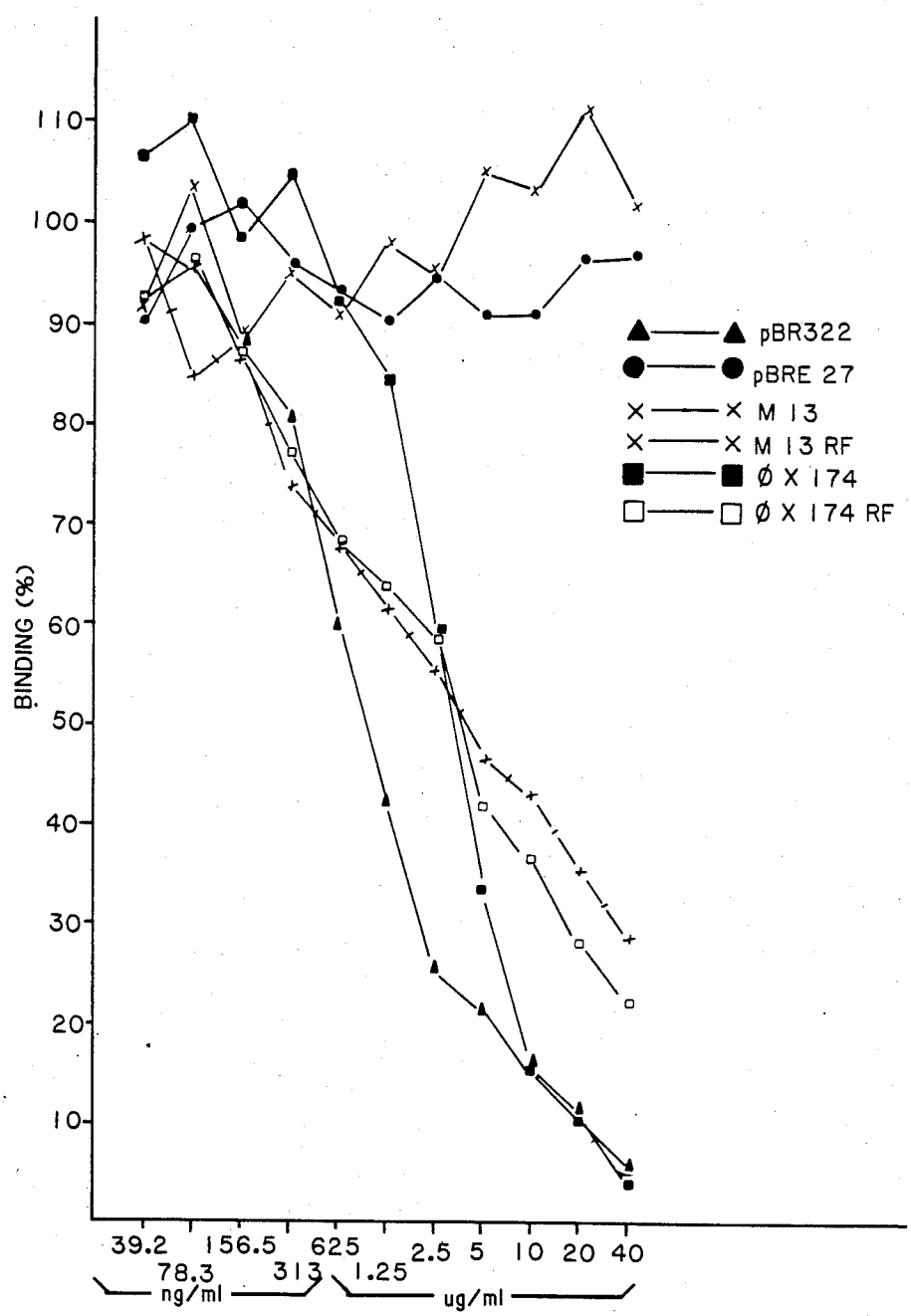
FIGS. 1A, 1B, and 2 are graphs of the results of blocking radioimmunoassay tests described in the examples.

The invention antibody recognizes the double-stranded conformation of native DNA as the immunodominant feature of the dsDNA molecule. In other words, the specificity of the determinant(s) the antibody recognizes is dictated by the double-stranded conformation of native dsDNA rather than by any sequence of nucleotides. The antibody recognizes native DNA duplexes re.g.ardless of the species of the DNA. Thus, as used herein the term "native" refers to dsDNA that occurs in nature and includes, without limitation, dsDNA derived from microorganisms, viruses, plants, fish, avians, and mammals or synthetic dsDNA, such as the duplexes in DNA probe technology, that is homologous or substantially homologous to naturally occurring dsDNA. The antibody does not bind to some synthetic dsDNA made from complementary homopolymeric strands of DNA.

While the monoclonal antibody that is specifically exemplified herein is a murine IgM, the invention is not limited to any particular species, class or subclass of immunoglobulin. Monoclonal antibodies of mouse, rat and human origin are currently preferred because of the availability of suitable mouse, rat and human cell lines to make the hybridomas that produce the antibody. Monoclonal antibodies of the same class or other classes such as IgG (including IgG subclasses such as IgG1, IgG2A, IgG3, etc), IgA, and IgD that are functionally equivalent to the murine IgM specifically exemplified herein may be made and identified by following the hybridoma synthesis and screening techniques described herein. As used herein the term "functional equivalent" is intended to mean a monoclonal antibody other than the exemplified murine IgM that also is native dsDNA specific. Preferred functional equivalents recognize the same determinant and cross-block the exemplified murine IgM.

If desired, the monoclonal antibodies may be derivatized (labeled) using conventional labeling reagents and procedures. As used herein the term "label" is intended to include both moieties that may be detected directly, such as radioisotopes or fluorochromes, and reactive moieties that are detected indirectly via a reaction that forms a detectable product, such as enzymes that are reacted with substrate to form a product that may be detected spectrophotometrically.

The antibodies may also be covalently coupled to chromatography supports (e.g., the surfaces of tubes or plates or the surfaces of particulate bodies such as beads) using available bifunctional coupling agents, such as carbodiimides, to make effective adsorbents for affinity purifying dsDNA. Such adsorbents may be used to isolate plasmids in the following manner. Bacteria containing the desired plasmid are lysed and their DNA is denatured. Lysing and denaturing may be done in a single step by suspending the cells in buffer at a high pH, e.g., 12.5. The resulting solution is then neutralized by adding cold buffer at pH 7-7.5. This will cause DNA duplexes to reform. Cellular debris is then removed from the solution by filtering or centrifugation. The filtrate/supernatant is then passed through a column containing the monoclonal antibody fixed to a support. Duplex plasmid DNA will be retained by the column and may be eluted therefrom with an appropriate elutant.

Kits for isolating plasmid DNA will contain the monoclonal antibody conjugated to the support, buffer for lysing bacterial cells and denaturing the DNA, a neutralizing buffer and an elution reagent.

The monoclonal antibodies of the invention may be made using the somatic cell hybridization procedure first described by Kohler, G. and Milstein, C., *Nature* (1975) 256:495-497. The tumor cell lines, reagents, and conditions used in this procedure are well known and have been reviewed extensively in the literature. (*Somatic Cell Genetics* (1979) 5:957-972 and *Monoclonal Antibodies* (1980) Plenum Press). Basically the procedure involves fusing an appropriate tumor cell line with cells (typically spleen cells) that produce the antibody of interest using a fusogen such as polyethylene glycol. Antibody-producing cells are typically made by immunizing a host with the immunogen of interest. In this regard the common source of anti-DNA antibodies are animals that have or are prone to have systemic lupus erythematosus (SLE) or similar diseases. Such animals spontaneously produce antibodies against DNA. Normal animals immunized with DNA are generally not considered to be good sources of anti-DNA antibody-producing cells. In making the murine IgM specifically exemplified herein, however, a normal mouse immunized with synthetic polynucleotide homopolymers (e.g., poly(dA·dT)·poly(dA·dT), poly(dI·dC)·poly(dI·dC), and poly(dG·dC)·poly(dG·dC)) and boosted with foreign native DNA were used as a source of anti-DNA antibody-producing spleen cells. These spleen cells are fused with a compatible myeloma line, such as line FO (*Transplantation Proc* (1980) Vol XII, No 3:447-450), that gives a high fusion frequency. After the fusion the conventional procedures of growing the fusion product in a selective growth medium, such as HAT medium, to eliminate unhybridized myeloma and spleen cells is followed. Clones having the required specificity are identified by assaying the hybridoma culture medium for the ability to bind to dsDNA and ssDNA. dsDNA+/ssDNA− clones may be further characterized by further specificity testing. Hybridomas that produce antibodies having conformation-dependent specificity for dsDNA may be subcloned by limiting dilution techniques and grown in vitro in culture medium or injected into host animals and grown in vivo. The antibodies may be separated from resulting culture medium or body fluids by conventional antibody fractionation procedures such as ammonium sulfate precipitation, DEAE cellulose chromatography, affinity chromatography and the like. The antibody may be further purified, if desired, by ultracentrifugation and microfiltration.

A principal use of the above-described anti-dsDNA monoclonal antibodies is to detect DNA duplex formation in diagnostic DNA hybridization tests similar to those described in U.S. Pat. No. 4,358,535. These methods are used in the field of medical diagnostics to determine the presence or quantity of a specific DNA molecule in a sample that characterizes a particular organism such as pathogenic bacteria, fungi, yeasts, or viruses or a genetic disorder such as sickle cell anemia or thalassemia. Such determinations permit the diagnosis of diseases, infections or disorders of the patient from which the sample is taken. They are also used to screen bacteria to determine antibiotic resistance and in gene mapping.

In these hybridizations a single-stranded polynucleotide probe is prepared that is complementary to a strand of the DNA of interest (e.g., the DNA that characterizes or differentiates the organism, disorder, condition, etc). This polynucleotide probe is then applied under hybridizing conditions to a sample suspected of containing the DNA of interest which has been treated so as to denature dsDNA in the sample and immobilize the resulting ssDNA. Immobilization is usually achieved by applying the sample to an insoluble material that has a high affinity for DNA, such as a nitrocellulose filter or other such inert porous support. Denaturation may be accomplished thermally or by treating the sample with a DNA denaturing agent. Alternatively, the complementary ssDNA probe could be immobilized and the denatured sample applied to the immobilized probe. The surface may be postcoated with an inert (nonhaptenic) material such as albumin to avoid nonspecific binding of other reagents to the support. Unhybridized materials are then removed and the hybridizate is assayed for the presence of nucleic acid duplexes. The absence of duplexes indicates the absence of the DNA of interest; positive detection of duplexes indicates the presence of the nucelic acid sequence of interest. In quantitative hybridization techniques, the amount of duplex formation is determined and is proportional to the amount of the DNA of interest in the sample.

The particular hybridization technique that is used is not critical to this invention. Examples of current techniques are those described in *PNAS* (USA) (1975) 72:3961-3965, PNAS (USA) (1969) 63:378-383; Nature (1969) 223:582-587 and the patent literature mentioned under "Background Art" above. The invention may be used with such procedures, and other existing hybridization procedures, as well as with hybridization procedures that are developed in the future.

In prior DNA hybridization procedures duplex detection was done by incorporating detectable moieties such as radioisotopes or biotin in the complementary polynucleotide probe. When the probe was hybridized with denatured sample DNA, the moieties in turn were incorporated into the resulting nucleic acid duplexes, making duplex detection possible. The monoclonal antibodies of the invention make it possible to avoid incorporating detectable moieties in the complementary polynucleotide probes. Correlatively they permit the polynucleotide probes to be made by cloning with single-stranded phage vectors such as bacterio-phages of the Ff group (e.g., M13, fd, fl) and $\phi$X 174, and derivatives thereof. Cloning with M13 or other single-stranded phage vectors provides the polynucleotide probe in large quantity (at least about 0.5 mg/L of culture) and high quality (pure with no breaks or ends). Use of higher concentrations of probe in the hybridization increases the sensitivity of duplex detection. This cloning procedure is commonly used to make ssDNA for use in the Sanger chain-termination method of DNA sequencing. These vectors and DNA cloning procedures employing them are described in *The Single-Stranded DNA Phages* (1978) Cold Spring Harbor Laboratory. Alternative methods for obtaining the complementary probe are available but they are not as efficient as cloning with single-stranded phage vectors. For instance dsDNA of proper sequence could be denatured beforehand or in situ, followed by restriction if necessary, and used in the hybridization.

The use of monoclonal antibodies in the detection phase of the DNA hybridization tests makes that phase equivalent to an immunoassay—with the duplex being the antigen to be detected. Accordingly, a variety of conventional immunoassay procedures may be used. Since the duplex will already typically be immobilized on a solid insoluble support, the antibody may be applied to the support, incubated under conditions that allow immune complex formation between the antibody and any immobilized duplex on the support, and the support washed to remove unbound antibody. Temperature, pH, and duration are the most important conditions in the incubation. The temperature will usually range between 5° C. and 40° C., the pH will usually range between 6 and 9 and the binding reaction will usually reach equilibrium in about 1 to 18 hr. Antibody will normally be used in excess. In instances where the antibody is labeled directly immune complexes may be detected via the label on the antibody. A more common and preferred procedure is to use unlabeled monoclonal antibody and incubate the immobilized dsDNA-monoclonal antibody complex with an enzyme-conjugated antibody against the monoclonal antibody. The same incubation conditions as were used in the initial incubation may be used. The resulting ternary complex may be treated with substrate and detected spectrophotometrically via the enzyme-substrate reaction. By using conventional procedures in which the detection means is bound indirectly to the dsDNA-monoclonal antibody via one or more layers of immunochemical it may be possible to amplify the detection signal to improve the sensitivity or the detection limit of the procedure.

The kits for carrying out the above described preferred hybridization tests will normally contain a DNA immobilizing material, a hybridization solution such as those described at column 5, lines 8-24 of U.S. Pat. No. 4,358,535, the ssDNA probe (either separate or pre-coated onto the immobilizing material), the monoclonal antibody, enzyme-conjugated antibody against the monoclonal antibody and an appropriate substrate. The kits may also contain a suitable buffer for dilution and washing, a dsDNA denaturing agent such as dilute aqueous NaOH, a post-coating preparation such as bovine serum albumin and directions for carrying out the tests. These components may be packaged and stored in conventional manners.

The following examples illustrate various aspects of the invention. These examples are not intended to limit the invention in any way.

Preparation of Monoclonal Antibody

A nine week-old female BALB/C mouse was immunized as follows:

| Day | Inoculant (administered ip) |
|---|---|
| 0 | 100 μg poly(dA-dT) + 100 μg mBSA in CFA |
| 14 | 100 μg poly(dI-dC) + 100 μg mBSA in ICFA |
| 23 | 50 μg poly(dA-dT) + 50 μg EcoRI digested pBR322 + 100 μg mBSA in PBS |
| 37 | 50 μg poly(dA-dT) + 50 μg EcoRI digested pBR322 + 100 μg mBSA in PBS | mBSA = methylated bovine serum albumin
CFA/ICFA = complete/incomplete Freund's adjuvant
PBS = phosphate buffered saline (0.14 M NaCl, 10 mM sodium phosphate, pH 7.0)

All polynucleotides used in the inoculation were puchased from P. L. Biochemicals, Inc., Milwaukee, Wis.

The mouse's spleen was removed on day 40. Spleen cells ($1.12 \times 10^8$) were fused with FO murine myeloma cells ($1.12 \times 10^8$) obtained originally from Dr. S. Fazekas de St. Groth, Basel Institute for Immunology, using the fusion and selection procedures described by Oi and Herzenberg in *Selected Methods in Cellular Immunology*, pp. 351-372.

Culture supernatants from wells containing surviving cells were screened for antibodies having conformation-dependent specificity for dsDNA using a solid phase enzyme-linked immunosorbent assay (ELISA) designed to evaluate binding to ssDNA and dsDNA. pBR322 restricted with EcoRI was used as the dsDNA and M13 single-stranded phage DNA was used as ssDNA. One hundred μl of solutions of these DNAs (10 μg/ml) in 0.1 M carbonate buffer, pH 9.8, were added to Immulon microtiter plates and incubated therein for 1-2 hr at room temperature. The plates were emptied and washed ($3 \times 200\mu l$) with PBS containing 0.05% Tween surfactant (PBS-Tween) and post-coated with a 1% solution of BSA in PBS for 10 min. One hundred μl of hybridoma culture supernatant was added to each well and incubated for one hr at room temperature. The plates were emptied and washed ($3 \times 200\mu l$) with PBS-Tween and 100 μl of goat anti-mouse Ig conjugated to alkaline phosphatase (Zymed Laboratories, South San Francisco, Calif.) was added to each well. After standing at room temperature for one hr, the wells were emptied and filled with 100 μl of one mg/ml p-nitrophenylphosphate in 10% diethanolamine buffer. The plates were incubated at 37° C. for about one hr. Absorbance (optical density, OD) at 405 nm was read using a microtiter plate reader (Micro ELISA Autoreader, Dynatech). OD readings higher than five times the control reading (medium instead of culture supernatant) are considered positive.

1459 Culture supernatants were screened in the above manner. Supernatant from one well, designated CH26-1352, reacted with the dsDNA but not with the ssDNA. The cells was expanded and subcloned by limiting dilution. A cloned sample of hybridoma CH26-1352 was deposited in the American Type Culture Collection, 12301 Park Lawn Drive, Rockville, Md. 20852, USA on August 3, 1983. This sample was assigned ATCC No HB 8329. Isotype analysis of the monoclonal antibody produced by hybridoma CH26-1352 indicated it is an IgM.

CH26-1352 Cells were injected intraperitoneally into Pristane-primed BALB/C mice. After 5–10 days, ascites were harvested from these mice. Both purified antibody from ascites and from culture supernatant were used in the specificity tests described below. The antibody was purified by dialyzing the ascites/supernatant against distilled water followed by centrifugation.

Additional Specificity Testing of Monoclonal Antibody Produced by Hybridoma CH26-1352

The specificity of monoclonal antibody CH26-1352 for the double-stranded conformation of DNA was confirmed by testing it in the above-described ELISA using another single-stranded phage DNA (φX 174, New England Biolab), and the following dsDNAs: replicative form (RF)I φX 174, RFII φX 174, calf thymus DNA, RF M13, and pBEU27. The antibody did not bind to ssφX 174 but bound to all five of the dsDNAs.

Blocking Radioimmunoassay (RIA)

Blocking RIAs were also carried out to illustrate the specificity of monoclonal antibody CH26-1352. Flexible polyvinylchloride microtiter plate wells were filled with 50 μl of a 25 μg/ml solution of the purified monoclonal antibody in carbonate buffer, 0.1 M, pH 9.8 and incubated for 2 hr at room temperature. The solution was then aspirated from the wells, the wells were washed (2×200 μl) with PBS-Tween, and post coated with 1% BSA in PBS (hereafter RIA buffer) for 10 min. Twenty-five μl of serial diluted DNA test samples (EcoRI-digested pBR322; pBEU27; ClaI-digested RFM13; M13; φX 174 RFφX174; λDNA; M13 containing a 1 kb pBR322 insert; M13 containing a 2.5 kb chlamydia insert; E. coli RNA; calf thymus DNA; and salmon testes DNA) in RIA buffer were added to the wells and the plates were shook for about one min. Twenty-five μl of $^{32}$P-labeled pBR322 prepared by nick translation was added to the wells and the contents were incubated for one hr at room temperature. The wells were then emptied and washed (3×200 μl) with PBS-Tween. The wells were cut and read with a scintillation counter. % Binding was calculated from the cpm readings using the formula:

$$\% \text{ Binding} = \frac{\text{cpm for test sample}}{\text{cpm for } RIA \text{ buffer}} \times 100$$

Figure 1B:
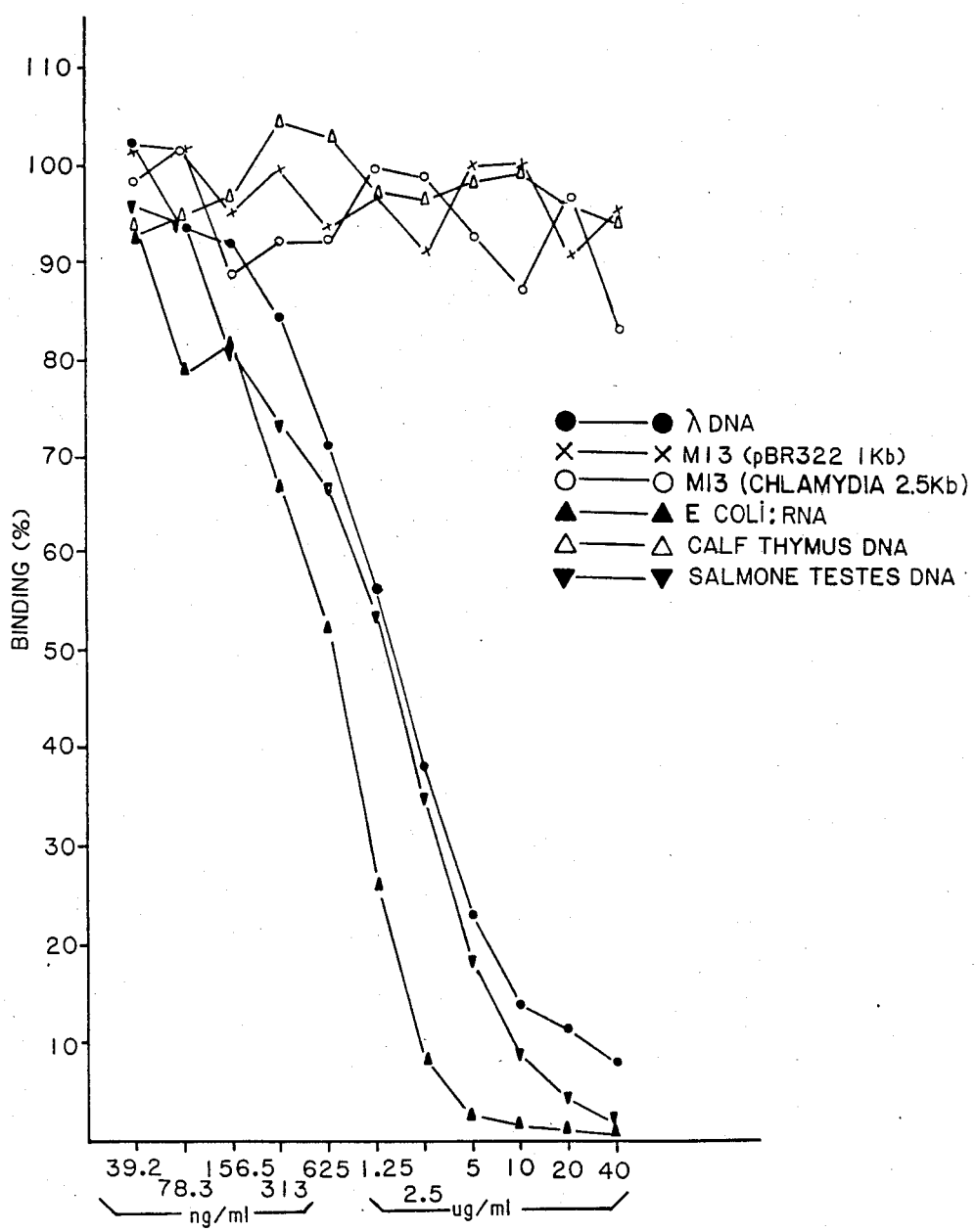

FIGS. 1A and 1B are graphs (% binding vs. dilution) of the results of these RIAs. As shown, no significant blocking of the $^{32}$P-labeled pBR322 was observed with the ssDNA and RNA samples. Blocking was observed with all dsDNA samples.

Figure 2:
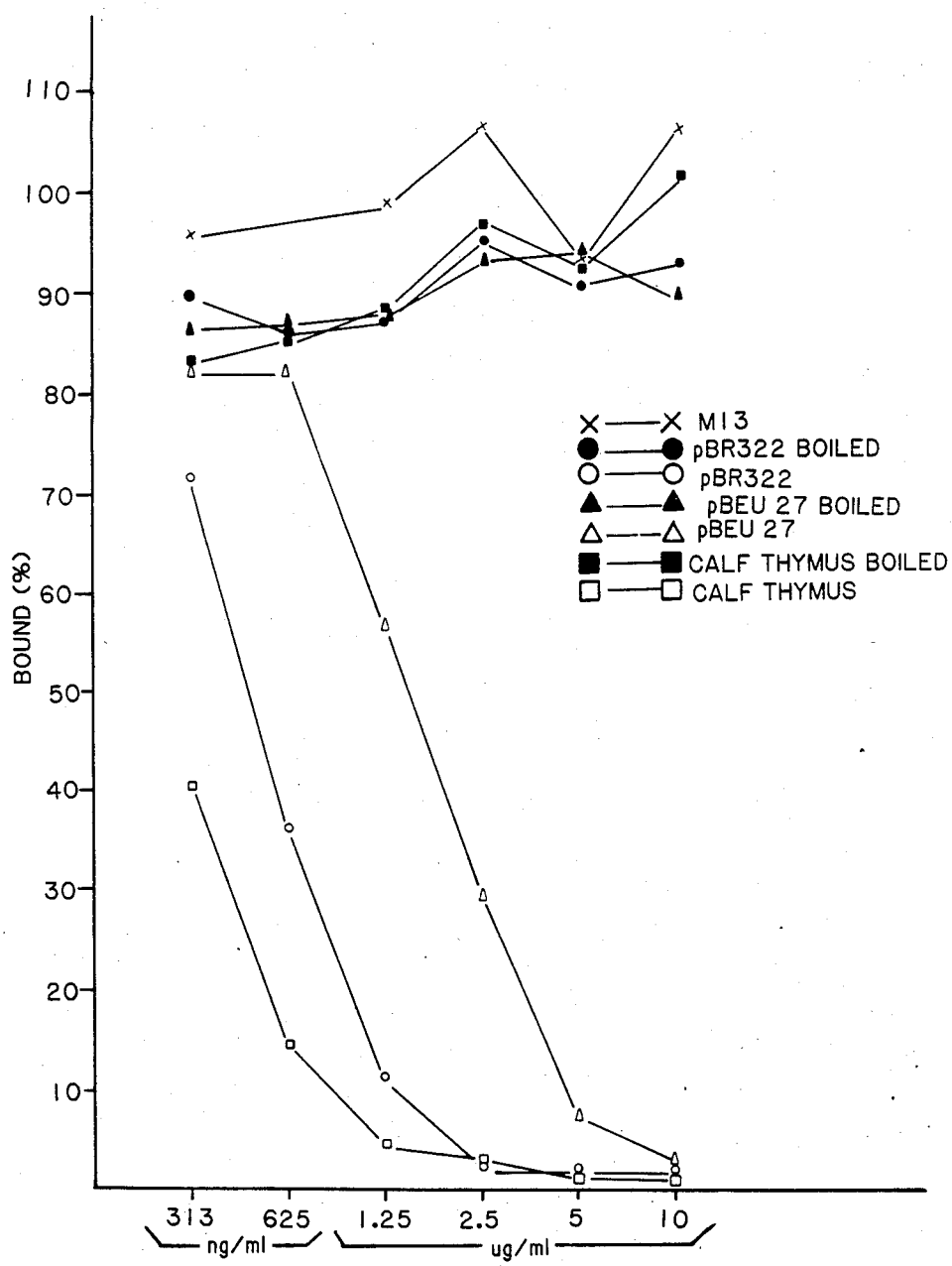

Blocking RIAs were also carried out using the above procedure on heat-denatured and nondenatured dsDNAs. The denatured dsDNA was made up by boiling 40 μg/ml solutions of the dsDNA in PBS for 15 min at 100° C. The boiled DNA was quick chilled in ice water and diluted ½× with cold RIA buffer. Serial dilutions of the denatured DNA were made as above. The DNA samples tested were: EcoRI digested pBR322, boiled; EcoRI digested pBR322, not boiled; EcoRI digested pBEU27, boiled; EcoRI digested pBEU27, not boiled; calf thymus DNA boiled; calf thymus DNA, not boiled; M13 013; M13 011. The results of these tests are reported in FIG. 2.

Blocking RIAs using the above procedure were carried out using various synthetic nucleic acid polymers as samples. The following polymers did not block $^{32}$P-labeled pBR322 binding:

| | |
|---|---|
| poly(dA-dT).poly(dA-dT) | poly(dG) |
| poly(dA-dU).poly(dA-dU) | poly(dC) |
| poly(dI-dC).poly(dI-dC) | poly(I) |
| poly(dA).poly(dT) | poly(dA) |
| poly(dA).poly(dU) | poly(dT) |
| poly(dI).poly(dC) | |

Positive reactivity was shown by poly(dG)·poly(dC), poly(I)·poly(dC), and poly(rG)·poly(dC) and weak positive reactivity by poly(dA-dC)·poly(dT-dG).

Solid Phase DNA/DNA Hybridizations Using M13 Probes and Monoclonal Antibody CH26-1352.

M13 containing fragments of pBR322 and λ DNA were used as probes. These probes were made by the "shotgun" M13 cloning procedure described in the BRL Instruction Manual for M13 Cloning/Dideoxy Sequences. See also PNAS (USA) (1977) 74:3642–3646 and Nature (London) (1978) 272:375–377. In this procedure pBR322 and λ DNA are restricted with a restriction enzyme that has a restriction site in the lacZ gene of mp9 (an M13 derivative). RFM13 is restricted with the same enzyme leaving it with compatible ends with those generated in the pBR322 and λ DNA fragments. The restricted DNAs are separated from the digest by phenol, phenol:CHCl$_3$ and CHCl$_3$ extraction followed by ethanol precipitation and are ligated. Recombinant DNA is distinguished from recircularized RFM13 by insertional inactivation of the lacZ gene due to the presence of the insert. In the presence of isopropyl-β-D-thiogalactopyranoside, recircularized RFM13 will form blue plaques on indicator plates containing X gal agar, whereas insert-containing M13 will form white (colorless) plaques. The following M13 probes were made: M13 containing a ~1/kb BamHI-PvuI pBR322 fragment (M13(pBR322)); M13 containing a 565 bp HindIII λ fragment (M13(λ#2)); and M13 containing a 2322 bp HindIII λ fragment (M13(λ#7)). M13 without any insert was also used as a control.

Immulon microtiter plate wells were filled with 100 μl of the M13 probe diluted (10 μg/ml) in 0.1 M carbonate buffer and incubated for 2 hr at room temperature. Wells filled with M13 were used as controls. The wells were emptied and washed (2×200 μl) with PBS-Tween and post-coated (2×200 μl) with RIA buffer at 37° C., 5 min each coating. pBR322 DNA and λ DNA were digested with HaeIII and HincIII, respectively and diluted at 10 μg/ml in 6×SSC hybridization buffer (6×SSC =0.02% Ficol, 0.02% polyvinyl pyrrolidine, 0.10% BSA, and 0.25% sodium dodecyl sulfate). The digested DNA was boiled for 10 minutes and diluted ½× in hot (~90° C.) 6×SSC buffer. Serial dilutions of the heat-denatured pBR322 and λ DNA samples (100 μl) were added to the wells, the plate was sealed and the sealed plate was incubated overnight at 68° C. The wells were then emptied and washed (3×200 μl) with PBS-Tween. One hundred μl of culture supernatant from hybridoma CH26-1352 was added to each well and incubated for 1 hr at room temperature. The wells were emptied and washed (3×200 μl) with PBS-Tween. One hundred μl of goat anti-mouse Ig conjugated to alkaline phosphatase was added to each well and incubated for 1 hr. One hundred μl of p-nitrophenylphosphate in 10% diethanolamine buffer was then added and the wells' contents were incubated at 37° C. for ½-1 hr. Absorbance at 405 nm was read as described above.

Specific hybridization between denatured λ DNA and M13 (λ#2) probe down to a dilution of 15.6 ng/ml denatured λ DNA was observed. Specific hybridizations between the denatured λ DNA and M13(λ#7) were observed down to 3.9 ng/ml denatured DNA. The greater sensitivity observed with the M13 (λ#7) probe is believed to be attributable to the fact that the insert of that probe is larger than the insert of M13(λ#2). Hybridizations between M13(pBR322) probe and denatured pBR322 DNA was observed down to about 3.9 ng/ml denatured DNA. No hybridization was observed between M13(pBR322) and denatured λ DNA. Some nonspecific binding between the M13(λ) probes and denatured pBR322 DNA occurred but the absorbance readings between these probes and denatured λ DNA were significantly higher than the readings between these probes and denatured pBR322 DNA. Some nonspecific binding between M13 probe and denatured pBR322 were observed but again, absorbance readings were significantly higher with the M13(pBR322) probe. No nonspecific hybridization between M13 probe and λ DNA was observed.

Modifications of the above described modes for carrying out the invention that are obvious to those of skill in the fields of immunochemistry, nucleic acid chemistry, immunodiagnostics, and related fields are intended to be within the scope of the following claims.

We claim:

1. Hybridoma ATCC HB 8329.

* * * * *